(12) United States Patent
Chen et al.

(10) Patent No.: US 9,357,972 B2
(45) Date of Patent: Jun. 7, 2016

(54) INTRAORAL RADIOGRAPHIC SENSORS WITH CABLES HAVING INCREASED USER COMFORT AND METHODS OF USING THE SAME

(71) Applicant: Cyber Medical Imaging, Inc., Los Angeles, CA (US)

(72) Inventors: Adam Chen, Pacific Palisades, CA (US); Douglas C Yoon, Beverly Hills, CA (US)

(73) Assignee: CYBER MEDICAL IMAGING, INC., Los Angeles, CA (US)

( * ) Notice: Subject to any disclaimer, the term of this patent is extended or adjusted under 35 U.S.C. 154(b) by 147 days.

(21) Appl. No.: 13/943,576

(22) Filed: Jul. 16, 2013

(65) Prior Publication Data

US 2014/0023177 A1     Jan. 23, 2014

Related U.S. Application Data

(63) Continuation-in-part of application No. 13/673,763, filed on Nov. 9, 2012.

(60) Provisional application No. 61/672,710, filed on Jul. 17, 2012.

(51) Int. Cl.
| | |
|---|---|
| *A61B 6/14* | (2006.01) |
| *H01L 27/146* | (2006.01) |
| *A61B 6/00* | (2006.01) |

(52) U.S. Cl.
CPC .............. *A61B 6/145* (2013.01); *A61B 6/425* (2013.01); *A61B 6/4233* (2013.01); *H01L 27/14618* (2013.01); *H01L 2924/0002* (2013.01)

(58) Field of Classification Search
CPC ............ A61B 6/14; A61B 6/145; A61B 6/42; A61B 6/4233; A61B 6/44; A61B 6/501; G01T 1/20; G01T 1/24; G01T 1/248; H04N 5/335

USPC ................ 378/62, 91, 167–169, 190–191
See application file for complete search history.

(56) References Cited

U.S. PATENT DOCUMENTS

| | | | |
|---|---|---|---|
| 4,350,886 | A | 9/1982 | Pommerrenig |
| 4,451,842 | A | 5/1984 | Pommerrenig |

(Continued)

FOREIGN PATENT DOCUMENTS

| | | |
|---|---|---|
| EP | 42604 B1 | 6/1981 |
| EP | 1259056 B1 | 9/1988 |

(Continued)

OTHER PUBLICATIONS

P. Maj. R. Szczygiel, et al; Readout Electronics for Pixel Detectors in Deep Submlcon & 3D Technologies; Intl. Journal of Electronics &Telecommunications, 2011,V57,#4, p. 497-502.

(Continued)

*Primary Examiner* — Robert Kim
*Assistant Examiner* — David E Smith
(74) *Attorney, Agent, or Firm* — Roy L. Anderson

(57) ABSTRACT

A radiological image sensor has an electronic substrate and an imaging chip held within a housing, the imaging chip having electronics that create a dead space, with a cable attached to the housing at a cable button connector, the dead space being at a short distal side of the generally rectangular sensor opposite the short mesial side at which the cable exits the cable button connector. The mesial side of the sensor either does not have a dead space created by electronics of the imaging chip or the dead space found on the mesial side of the sensor is less than approximately 4 mm, and, preferably, approximately 2 mm or less. The cable can be a flat cable with a length of approximately one meter or less that can be connected to a round cable.

13 Claims, 7 Drawing Sheets

(56) References Cited

U.S. PATENT DOCUMENTS

| | | | |
|---|---|---|---|
| 5,434,418 A * | 7/1995 | Schick | G01T 1/2018 250/370.09 |
| 5,510,623 A * | 4/1996 | Sayag | G01T 1/2928 250/208.1 |
| 5,691,539 A * | 11/1997 | Pfeiffer | 250/370.09 |
| 6,169,781 B1 | 1/2001 | Doebert et al. | |
| 6,654,064 B2 | 11/2003 | Ishikawa | |
| 7,050,538 B2 | 5/2006 | Tashiro et al. | |
| 7,663,115 B2 | 2/2010 | Korthout | |
| 7,916,200 B2 * | 3/2011 | Ligozat | A61B 6/145 348/315 |
| 7,952,077 B2 | 5/2011 | Tashiro et al. | |
| 2004/0114725 A1 * | 6/2004 | Yamamoto | 378/189 |
| 2006/0028546 A1 | 9/2006 | Yersin | |
| 2006/0237625 A1 * | 10/2006 | Caupain | H01L 27/1463 250/208.1 |
| 2006/0257816 A1 * | 11/2006 | Klemola | A61B 6/4233 433/29 |
| 2010/0141820 A1 | 6/2010 | Chenebaux et al. | |
| 2011/0013745 A1 * | 1/2011 | Zeller | A61B 6/145 378/91 |

FOREIGN PATENT DOCUMENTS

| | | |
|---|---|---|
| EP | 714038 B1 | 11/1995 |
| EP | 729269 A1 | 1/1996 |
| EP | 1049171 B1 | 7/1999 |
| EP | 1188187 B1 | 5/2000 |
| EP | 1173007 B1 | 7/2001 |
| EP | 2290952 A2 | 7/2001 |
| EP | 1483790 B1 | 2/2003 |
| EP | 2103958 A2 | 5/2005 |
| EP | 1623673 | 2/2006 |
| EP | 1913645 B1 | 8/2006 |
| EP | 2 077 583 A1 | 10/2007 |
| EP | 2305119 A1 | 6/2009 |
| WO | WO 9428583 A1 | 5/1994 |
| WO | WO 96/32084 | 10/1996 |
| WO | WO 9632064 A1 * | 10/1996 |
| WO | WO 02076155 A1 | 9/2002 |
| WO | WO 03077538 A2 | 3/2003 |
| WO | WO 2005034241 A1 | 4/2005 |
| WO | WO 2007041078 A1 | 9/2006 |
| WO | WO 2008013607 A2 | 1/2008 |

OTHER PUBLICATIONS

Ying Huang et al; Component Level Modular Design of a Solid State X-ray Image Intensifier for an MxN Array, IEEE Nuclear Science Symposium, 2010, p. 2714-2717.

Zheng Li, et al; Novel Silicon Stripixel Detectors on High Resistivity p-type Magnetic Czochralski Silicon Wafter for US-ATLAS Upgrade; IEEE , 2004 Symposium, V2, 912-16.

Zheng Li, et al; Electrical and TCT Characterization of Edgeless Si Detectors Diced with Different Methods; IEEE Symposium, 2002 V1, 202-6.

Zheng Li, et al; Electrical and TCT Characterization of Edgeless Si Detectors Diced with Different Methods; IEEE Symposium, 2001, V.1, 202-6.

Sherwood I. Parker, et al; 3DX:An X-Ray Pixel Array Detector with Active Edges; IEEE Symposium Transactions on Nuclear Science, V53, n3,pt.3,1676-88, Jun. 2006.

Hugh T. Philipp, et al; Pixel Array Detector for the Capture of Femtosecond Duration X-ray Images; Ultrafast X-Ray Sources & Detectors conference; SPIE vol. 6703, 67030O, 2007.

* cited by examiner

Mesial End     Distal End

Mesial End     Distal End

INTRAORAL RADIOGRAPHIC SENSORS WITH CABLES HAVING INCREASED USER COMFORT AND METHODS OF USING THE SAME

CROSS REFERENCE TO RELATED APPLICATIONS

This application is a non-provisional application which claims priority from U.S. Ser. No. 61/672,710, filed Jul. 17, 2012, the disclosure of which is specifically incorporated herein by reference. This application is also a continuation-in-part of U.S. Ser. No. 13/673,763, filed Nov. 9, 2012, the disclosure of which is also specifically incorporated herein by reference.

FIELD OF THE INVENTION

The present invention is in the field of intraoral radiographic sensors and their methods of use and, more particularly, to increasing patient comfort during such use.

BACKGROUND OF THE INVENTION

Radiographs are fundamental to most dental diagnostic procedures. However, a common complaint and problem during radiographic exams is patient discomfort during the placement of radiographic sensors within the mouth. The majority of these complaints involve the placement of the radiographic sensor in the posterior maxillary and mandibular arches of the patient. This problem is primarily due to the limited space available for proper placement of the sensors within these regions. This has been a problem since the inception of dental radiography using standard x-ray film technology.

Recently, solid-state x-ray sensors have been developed that replace film. The patient discomfort problem for these sensors is even greater because these devices are rigid by nature and cannot be bent like film to conform to the patient's anatomy.

As noted in U.S. Pat. No. 7,916,200, the disclosure of which is specifically incorporated herein by reference, a radiological imaging sensor normally comprises a semiconductor chip having a matrix of photosensitive members and linked electronic circuits, a printed circuit board on which the chip and possibly some other components are mounted, a scintallator covering the chip, and occasionally a fiber-optic plate inserted between the scintillator and the chip. The unit is contained in a resin package from which a connection cable may extend to a system for processing the collected images (except in the case of wireless transmission, in which case a battery is provided, as a rule, in the package). The package conforms as closely as possible to the shape of the chip so as not to create unnecessary bulk. The shape of the chip which is, a priori, rectangular requires the package to have a rectangular shape, which is neither ergonomic nor comfortable for the patient.

The present invention is primarily concerned with radiological imaging sensors that include a connection cable and are not wireless, but the same concepts can be applied to wireless sensors as well. Because of patient discomfort during imaging of specific anatomic areas like standard bitewing or periapical views for periodic recall radiographs, there is much room and a long felt need for improvement in the design of such sensors. It is this problem, of patient discomfort, to which this invention is primarily directed. If the design of radiological image sensors is improved, with greater patient comfort, they will be easier to work with, potentially yielding better radiographs, with all of the concomitant benefits that can be obtained by improved dental diagnostic procedures, thus benefiting not only patients and the dental industry, but also society as a whole.

SUMMARY OF THE INVENTION

The present invention is generally directed to a radiological imaging sensor which comprises in part an electronic substrate and an imaging chip held within a housing, the imaging chip having electronics that create a dead space on the surface area adjacent to the active area which includes two corner portions of added local free space.

A cable is attached to the housing at a cable button connector on the non active side of the sensor, the dead space located along the short distal side of the generally flat rectangular sensor opposite the short mesial end at which the cable exits the cable button connector.

This mesial imaging area is crucial for imaging the distal aspect of the canine teeth and the mesial aspect of the first premolars in the bitewing radiograph.

In one group of separate aspects of the present invention, the mesial side of the sensor either does not have a dead space created by electronics of the imaging chip or the dead space found on the mesial side of the sensor is less than approximately 4 mm, and preferably, approximately 2 mm or less, except for the two corner portions of added local free space.

In another group of separate aspects of the present invention, the cable is a flat cable with a length of approximately but not limited to one meter or less that can be connected to a round cable by a cable connector and the cable button connector is mounted to the housing more distant to the mesial side than to the distal side.

Accordingly, it is a primary object of the present invention to provide an improved intraoral radiographic sensor that can be used to obtain better radiograph images of some teeth.

This and further objects and advantages will be apparent to those skilled in the art in connection with the drawings and the detailed description of the invention set forth below.

BRIEF DESCRIPTION OF THE DRAWINGS

FIGS. 6 and 7 illustrate sensor internal free space and shock absorber area in a radiological image sensor while

DETAILED DESCRIPTION OF THE INVENTION

Figure 1:
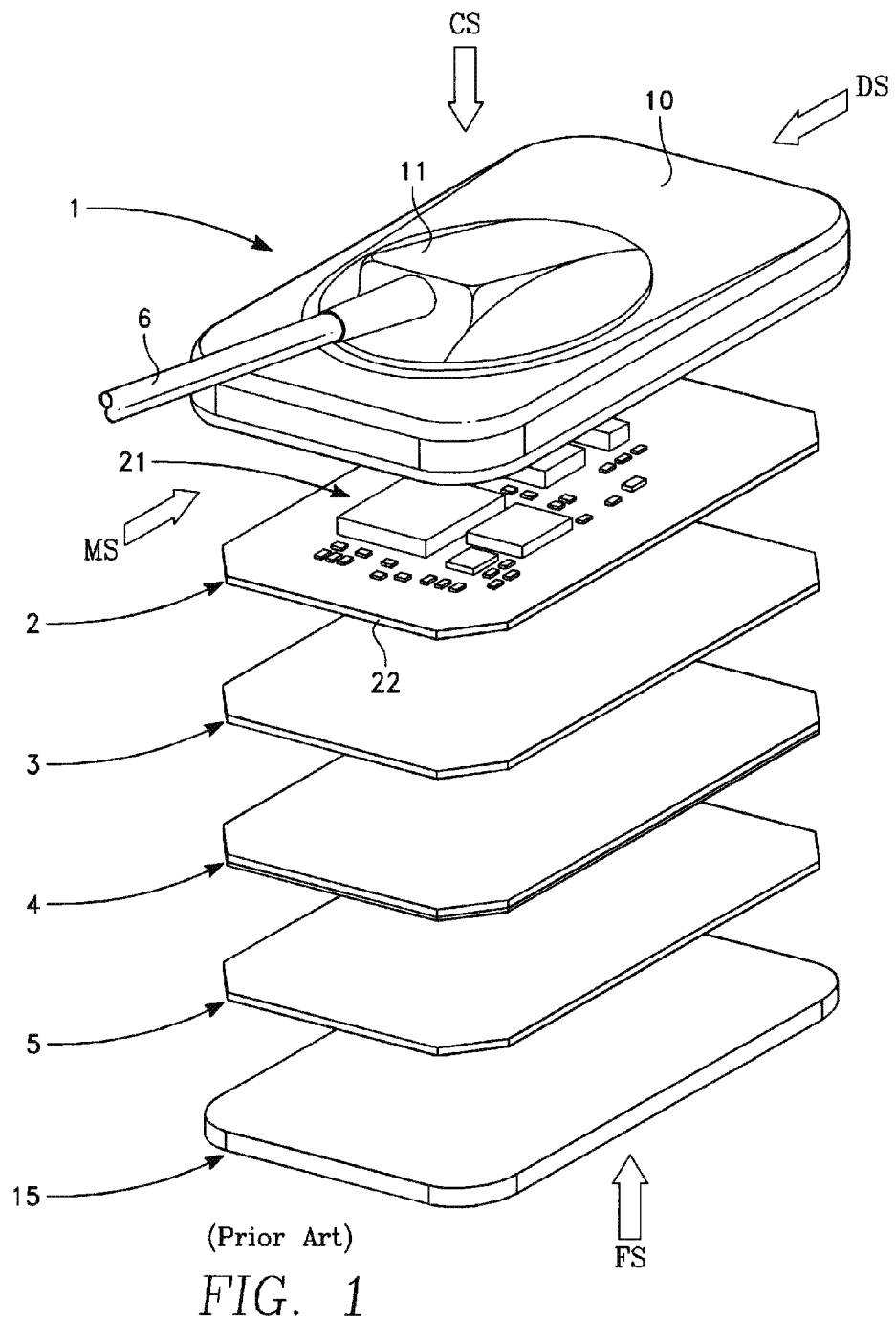
FIG. 1 is a partial assembly view that illustrates a prior art radiological image sensor and its primary components.
Figure 1A:
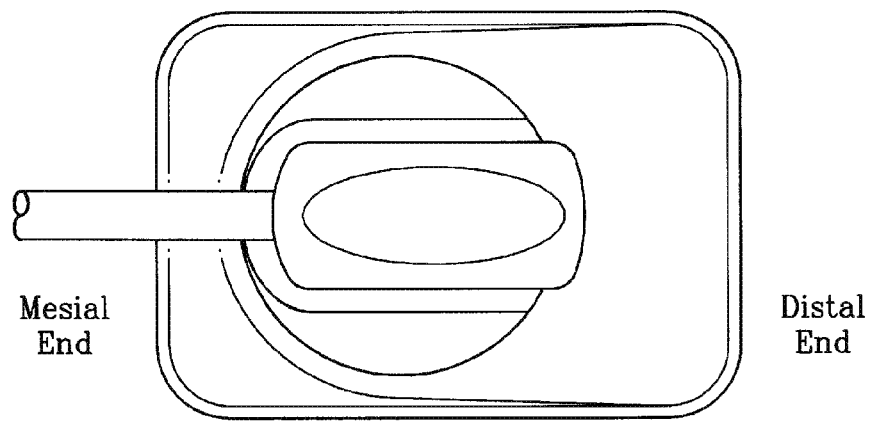
FIG. 1A is a photograph of a prior art radiological image sensor showing the orientation between distal and mesial and FIG. 1B is a radiograph of the sensor shown in FIG. 1A that illustrates the dead space on the mesial end of a typical traditional sensor.
Figure 1B:
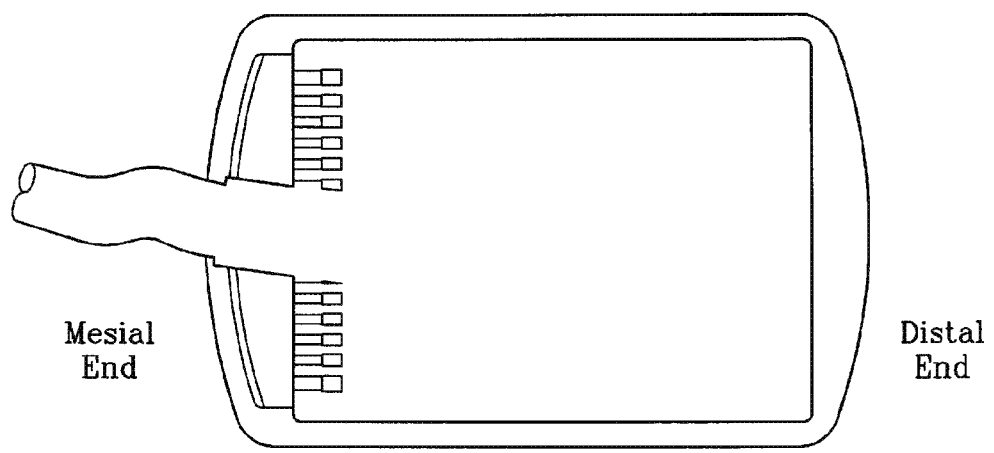

The following glossary is used for the Figures and description which follows herein:

Glossary
1 radiological image sensor
2 electronic substrate
3 imaging chip
4 fiber optic face plate
5 CSI scintillator
6 cable
8 dead space attributable to shock absorption material and housing
9 dead space attributable to electronic components 31
10 cable side housing
11 cable button connector
15 front side housing
21 electronic components
22 ceramic material
31 electronic components
40 flat cable
41 round cable
42 connector
CS cable side
DS distal side
FS front side
MS mesial side FIG. 1 illustrates a prior art radiological image sensor 1 that has a cable side housing 10 connected to a front side housing 15 with a cable 6 running out of cable button connector 11 in front side housing 15 toward mesial side MS of sensor 1. Inside the housing, moving from cable side CS down to front side FS, are an electronic substrate, shown generally as 2 (preferably comprised of electronic components 21 mounted on the cable side of ceramic material 22), an imaging chip, shown generally as 3 (preferably a CMOS imaging chip), a fiber optic face plate, shown generally as 4 (which functions as an x-ray filter for improved noise reduction), and a CSI scintillator, shown generally as 5 (optimized for resolution and low noise).

Sensor 1 has a generally rectangular shape, as illustrated in FIG. 1. For purposes of the present invention, the shorter sides of the rectangle will always be defined by the direction in which cable 6 exits cable button connector 11. Mesial side MS (see FIG. 1) will always be defined as the side toward which cable 6 exits cable button connector 11 while distal side DS will always be defined as the side opposite which cable 6 exits cable button connector 11, even if cable button connector 11 is not centered in cable side housing 10 (see FIG. 2).

Figure 2:
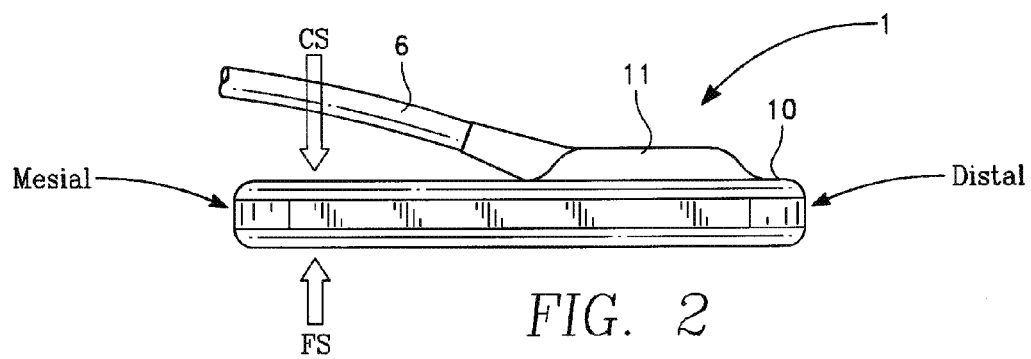
FIG. 2 is a side view of a sensor showing a cable button connector located more proximate its distal side than its mesial side.

In accordance with the present invention, it is especially preferred that cable button connector 11 be located more proximate distal side DS than centered (see FIG. 2). The reason such placement is preferred is that it allows more room for cable 6 coming out of cable button connector 11 to twist or turn when the sensor is used in some locations of a patient's mouth, thus reducing stress on the connection between cable 6 and cable button connector 11, which must be watertight.

In typical prior art sensors, electronic substrate 2 has a shock absorption material (not shown) around the periphery of ceramic material 22. The space occupied by shock absorption material, as well as space occupied the sensor housing (once cable and front side housings 10 and 15 are assembled together), creates a dead space 8 (see FIG. 3) in which a radiographic image is not obtained, and the size of this dead space will typically be no less than 2 mm. In addition to dead space 8, a second dead space 9 is created by electronic components 31 located on mesial side MS of imaging chip 3 in presently available sensors, which can represent another 4 mm or more of additional dead space.

The combined effect of dead spaces 8 and 9 in currently available intraoral radiographic sensors is an inability to duplicate the same coverage area in a patient's oral anatomy as x-ray film when placed in the exact same position relative to the patient's teeth. This problem is due to the intrinsic design and layout of all digital intraoral sensors, with regard to the placement of the dead space, which is created as a by-product by parts of the electronic on the sensor. Significantly, this 4-8 mm dead space is approximately the width of half to a whole canine, or premolar tooth, as shown in FIG. 4.

Figure 4:
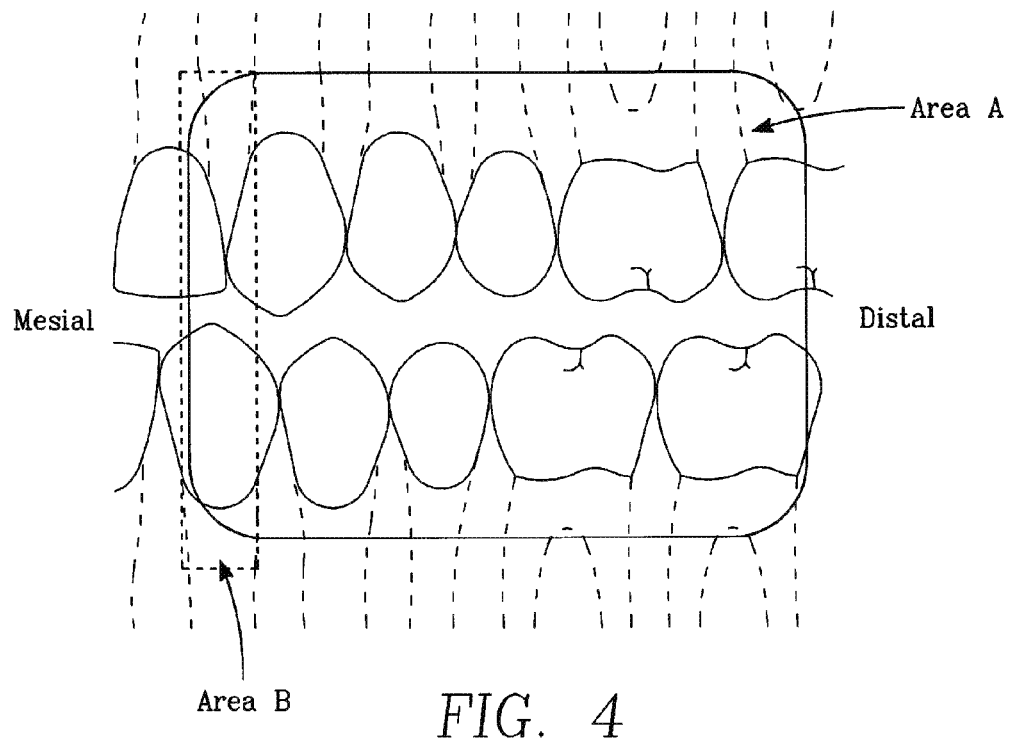
FIG. 4 illustrates typical loss of imaging area due to dead space for sensor electronics for a typical digital sensor.

FIG. 4 illustrates a coverage Area A for a standard premolar bitewing film radiograph. Within Area A, at its mesial side, is another Area B. Area B illustrates a typical loss of imaging area due to dead space for sensor electronics for a digital sensor. Accordingly, FIG. 4 illustrates that if a digital dental sensor is placed in the exact position as the x-ray film, the resultant image will not show the first 4-8 mm of the mesial end of the patient's anatomy.

Figure 3:
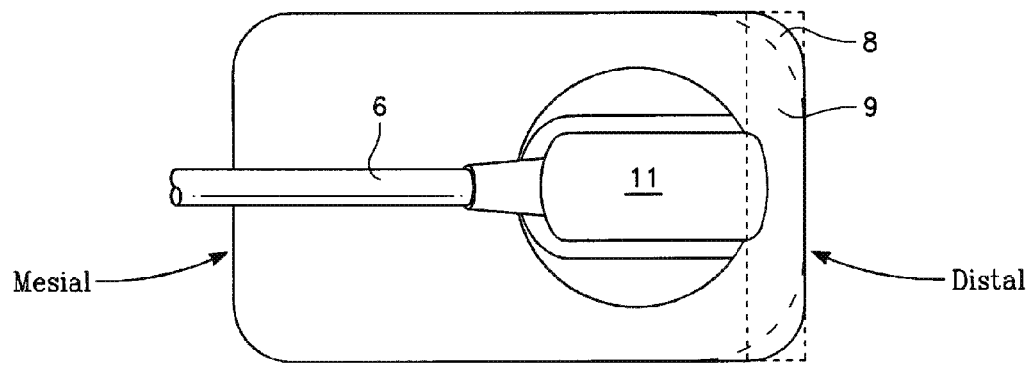
FIG. 3 is a top view cutaway of the sensor of FIG. 2 showing certain aspects of a sensor in accordance with a preferred embodiment of the present invention, flat cord exiting the sensor button at a more distal position, with the sensor dead space located at the distal end of the sensor.

However, in accordance with one aspect of the present invention, dead space 9 is moved to distal side DS of imaging chip 3 so that any dead space located on the mesial side of the sensor is kept to a bare minimum attributable solely to shock absorption material and the housing. Such a sensor design is shown in FIG. 3 which illustrates a cable side view of an electronic substrate 2 according to the present invention with dead space 9 being located at distal side DS, not mesial side MS. For purposes of orientation, cable 6 and cable button connector 11 are shown as trace lines in FIG. 3.

Locating dead space 9 at distal side DS, contrary to current practices and traditional wisdom, allows a dental practitioner to capture images not currently obtainable because Area B of FIG. 4, which represents a loss of imaging area due to dead space, is minimized, thus allowing greater capture of teeth located in the mesial area of a radiograph capture, which is especially important when a bitewing or periapical radiograph is being taken of the canine and premolar teeth.

In this regard, some of the most painful radiographs captured are the premolar bitewing and posterior periapical views. The reason these radiographs are painful to take is that the imaging plate, whether a film or a sensor (which is stiffer and can cause more pain), must be located such that its mesial end is placed as far forward in the patient's mouth as possible to capture the distal aspect of the canine teeth and the mesial aspect of the premolar teeth in a bitewing or periapical view radiograph; and once the patient bites down the edges of the film or sensor dig into the tissue on the anterior ascending aspect of the maxillary palate or the lingual aspect of the anterior mandibular region; thus often causing pain when the mesial aspect of the digital sensor is impinging against these very sensitive anatomic regions during a radiographic exam. When a radiograph is being taken with a sensor with a cord, the sensor must be inserted to that the distal end is located towards the distal aspect of the teeth being imaged and then the mesial end is located at most mesial aspect of the teeth being imaged. By minimizing dead space at the mesial end MS of a sensor, the procedure for obtaining a radiograph of the patient's posterior teeth is far more comfortable and less painful, and better results are obtained.

Accordingly, a sensor in accordance with the present invention, in which dead space in its mesial end is minimized, represents a significant advance over the prior art and allows dental practitioners to obtain much better radiographs of all teeth being radiographed.

Another aspect of the present invention focuses on minimizing discomfort associated with obtaining radiographs of teeth with radiological image sensors that include a connection cable by changing the shape of the connection cable from round or circular to an asymmetric shape that is substantially wider than its height, preferably at least two or more times wider than its height, examples of which might be ovoid or flat. Such an improved cable, for the remainder of this description, will be referred to as a flat cable.

A flat cable according to the present invention will be easier to fit to a patient's mouth while certain radiographs are taken because it reduces cord bulk and bite interference. Rather than having to bite down with a circular cord running out between the patient's teeth, the patient will now have to bite down on a flat cord that creates less of a gap between teeth, thus increasing comfort and imaging coverage of the sensor. Also, use of a flat cord may reduce the thickness of cable button connector 11, which should also increase patient comfort and easier placement of the sensor in the patient's mouth.

Accordingly, a sensor in accordance with the present invention, in which a flat cord is implemented represents a significant advance over the prior art and allows dental practitioners to obtain much better radiographs of all teeth being radiographed and increased patient comfort.

Current connection cables are round and designed to meet applicable standards for USB connections as well as UL and other applicable standards. The desire to meet USB standards stems, at least in part, for ease of use and the ability to quickly and easily connect with computers.

A flat cable suitable for use in the present invention can meet USB standards, but it need not necessarily do so. The key design criteria is to reduce the thickness of the flat cable that must fit between upper and lower teeth when certain radiographs are being taken.

Figure 5:
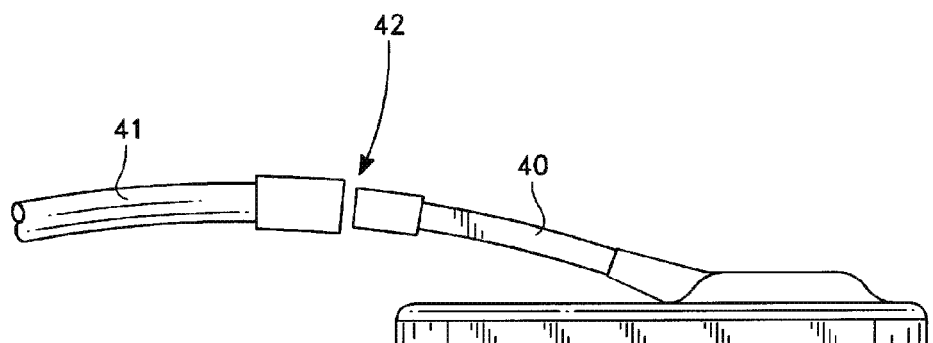
FIG. 5 illustrates one embodiment of a flat cable useful in a digital sensor according to the present invention.
Figure 6:
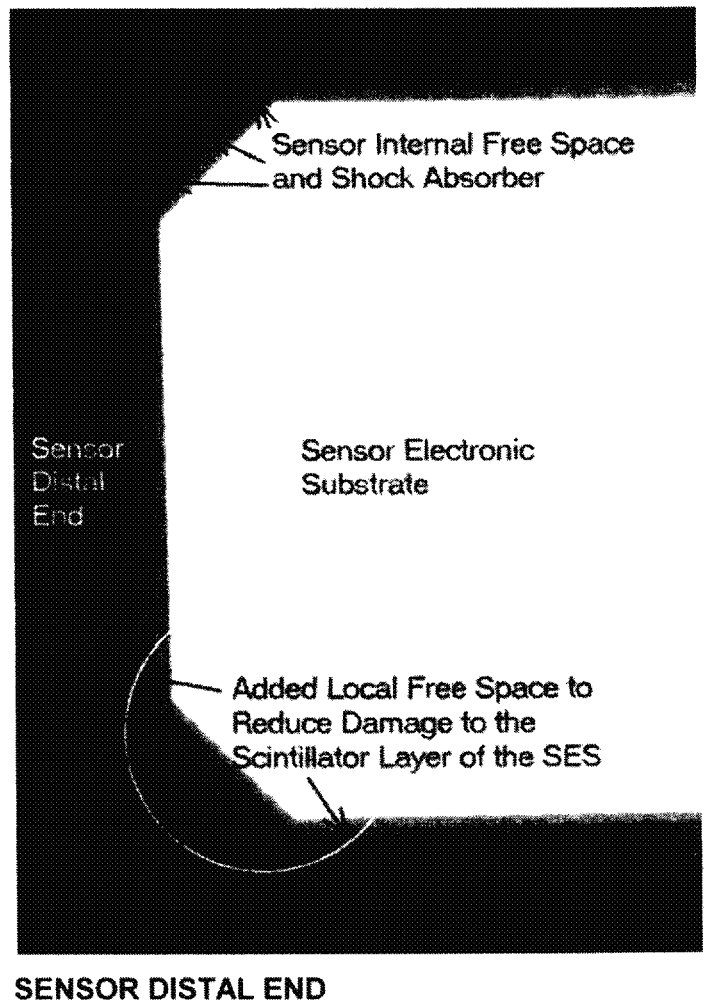
Figure 7:
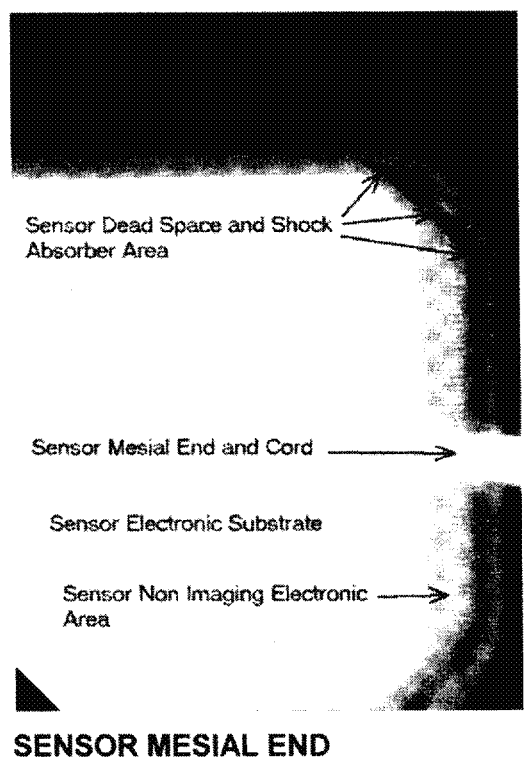

One possible alternative of a flat cable suitable for use in the present invention uses a short flat cable 41, with a length of approximately one meter or less (not shown to scale), that can be connected to a round USB compliant cable 42 by a small connector 43, an example of which is illustrated in FIG. 5.

Such a design has several advantages. First, it provides electrical isolation. Second, it allows for ease of conversion to USB. Third, it provides a more easily replaceable and/or repairable cord, because the longer cord can easily be replaced.

When a flat cord is combined with reduced dead space in the mesial end of a sensor, the result is a much improved sensor which provides increased comfort in a patient's mouth, improved image coverage at the mesial end, reduced stress on the cord attachment to the sensor housing, improved cord durability and reduce cord bulk and interference.

Another improvement in a radiological imaging sensor will now be described.

As has already been mentioned, the present invention is generally directed to a radiological imaging sensor which comprises an electronics substrate and an imaging chip held within an external housing or shell, the imaging chip having a specific shape and size. The shape of the electronic substrate will dictate the general shape and dimensions of the external housing or shell and it's internal dimensions. Inside the sensor shell there is also internal free space for the mounting of shock absorbing structures and for the compression of the shock absorbing structures and resultant movement of the electronic substrate when the sensor is subjected to shock. In particular, the scintillator layer on the electronic substrate is very sensitive to shock, which can result in irreversible damage and result a concomitant defect in the radiographic image.

Figure 8:
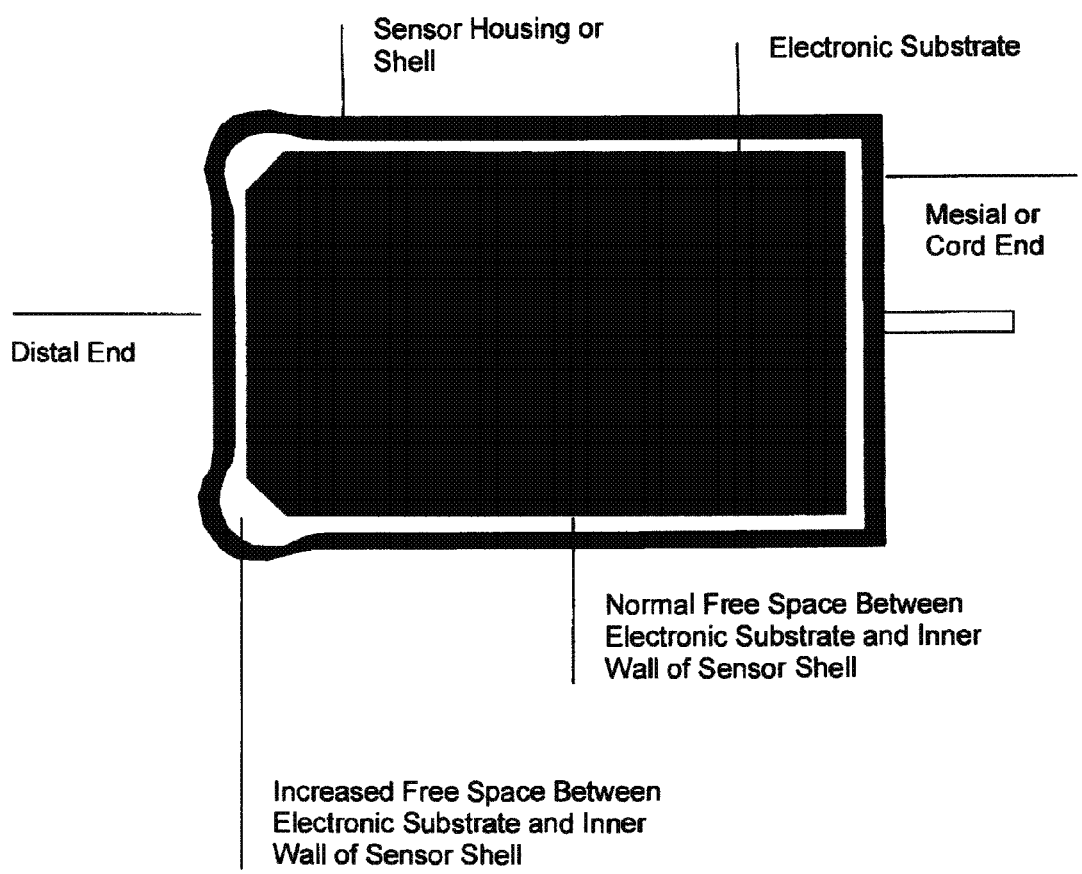
FIG. 8 illustrates an improved embodiment of such a sensor in accordance with the present invention.

Traditionally, to increase the free space that surrounds the delicate electronics designers uniformly increase the entire internal and external dimensions of sensor housing in order to maintain uniform rectilinear dimensions of the overall sensor package. Such an approach is easy to design and easy to fabricate. However, shock damage to the scintillator layer is usually limited to the four corners of the electronic substrate, and specifically to the two corners located at the sensor's distal end. This is mainly due to the fact that the sensor has an attached cable, therefore, when the sensor is accidentally dropped, the end which will impact first is usually biased toward the distal (non cable end) of the sensor and usually impacts on the corner. Traditionally, this type of scintillator damage can be reduced by increasing the internal free space between the electronic substrate and the internal sides of the sensor shell which will result in an increase of the overall size of the sensor shell. Because this type of damage tends to be biased to the two distal corners, a sensor shell design that increases the free space only in a local region adjacent to the corners of the electronic substrate can decrease the probability of shock damage without increasing the overall size of the sensor shell. This local increase of the free space at two or more corners of the sensor shell can be achieved by either increasing both the external and internal dimension (resulting in a local bulge of the sensor housing such as is illustrated in FIG. 8), or only in the internal dimension of the sensor shell (resulting in no external bulge in the sensor housing but rather an internal expanded pocket). This concept of local bulging or internal pocketing of the sensor housing can be applied to other sensitive structures on the electronic substrate such as on the flat back surface holding delicate electronics.

While the invention has been described herein with reference to certain preferred embodiments, those embodiments have been presented by way of example only, and not to limit the scope of the invention. Additional embodiments thereof will be obvious to those skilled in the art having the benefit of this detailed description.

Accordingly, it will be apparent to those skilled in the art that still further changes and modifications in the actual concepts described herein can readily be made without departing from the spirit and scope of the disclosed inventions.

What is claimed is:

1. A radiological image sensor, comprising:
    an electronic substrate and an imaging chip held within a housing, said imaging chip having electronics that create a dead space; and
    a cable attached to the housing at a cable button connector;
    wherein the sensor has a generally rectangular shape with a short mesial side toward which the cable exits the cable button connector and a short distal side opposite which the cable exits the cable button connector; and
    wherein the dead space is created in the distal side of the sensor and the dead space includes two corner portions of added local free space.

2. The radiological image sensor of claim 1, wherein the mesial side of the sensor does not have a second dead space created by electronics of the imaging chip.

3. The radiological image sensor of claim 1, wherein the sensor has a mesial side dead space of less than approximately 4 mm.

4. The radiological image sensor of claim 1, wherein the sensor has a mesial side dead space of approximately 2 mm or less except for the two corner portions of added local free space.

5. The radiological image sensor of claim 1, wherein the cable is a flat cable.

6. The radiological image sensor of claim 5, wherein the cable button connector is mounted to a cable side of the housing more distant to the mesial side than to the distal side.

7. A radiological image sensor, comprising:
an electronic substrate and an imaging chip held within a housing, said imaging chip having electronics that create a dead space; and
a cable attached to the housing at a cable button connector;
wherein the sensor has a generally rectangular shape with a short mesial side toward which the cable exits the cable button connector and a short distal side opposite which the cable exits the cable button connector; and
wherein a majority of the dead space is created in the distal side of the sensor.

8. The radiological image sensor of claim 7, wherein the mesial side of the sensor does not have a second dead space created by electronics of the imaging chip.

9. The radiological image sensor of claim 7, wherein the sensor has a mesial side dead space of less than approximately 4 mm.

10. The radiological image sensor of claim 7, wherein the sensor has a mesial side dead space of approximately 2 mm or less except for the two corner portions of added local free space.

11. The radiological image sensor of claim 7, wherein the cable is a flat cable.

12. The radiological image sensor of claim 11, wherein the cable button connector is mounted to a cable side of the housing more distant to the mesial side than to the distal side.

13. A method for capturing a premolar bitewing or posterior periapical view radiograph through use of an intraoral radiological imaging sensor having an imaging chip held within a housing, comprising the steps of:
locating the intraoral radiological imaging sensor such that its mesial end is placed as far forward in the patient's mouth as possible to capture the distal aspect of the canine teeth and the mesial aspect of the premolar teeth in a bitewing or periapical view radiograph; and
obtaining the radiograph;
wherein there is substantially no dead space at the mesial end of the intraoral radiological imaging sensor due to imaging chip control electronics for an active pixel array of the imaging chip.

* * * * *